US00PP19868P2

(12) United States Plant Patent
Ruys

(10) Patent No.: US PP19,868 P2
(45) Date of Patent: Mar. 31, 2009

(54) ***MANDEVILLA* PLANT NAMED 'SUNPARADAI'**

(50) Latin Name: *Mandevilla hybrida*
Varietal Denomination: Sunparadai

(75) Inventor: Theo Ruys, Leimuiderbrug (NL)

(73) Assignee: Suntory Flowers Limited, Tokyo (JP)

( * ) Notice: Subject to any disclaimer, the term of this patent is extended or adjusted under 35 U.S.C. 154(b) by 0 days.

(21) Appl. No.: 12/079,408

(22) Filed: Mar. 25, 2008

(51) Int. Cl.
*A01H 5/00* (2006.01)

(52) U.S. Cl. ..... Plt./232
(58) Field of Classification Search ..... Plt./232
See application file for complete search history.

*Primary Examiner*—Annette H Para
(74) *Attorney, Agent, or Firm*—C. A. Whealy

(57) ABSTRACT

A new and distinct cultivar of *Mandevilla* plant named 'Sunparadai', characterized by its upright and vining plant habit; relatively small glossy foliage; freely branching habit; freely flowering habit; dark red purple-colored flowers; and long flowering period.

1 Drawing Sheet

Botanical designation: *Mandevilla hybrida.*
Cultivar denomination: 'Sunparadai'.

BACKGROUND OF THE INVENTION

The present invention relates to a new and distinct cultivar of *Mandevilla,* botanically known as *Mandevilla hybrida* and hereinafter referred to by the name 'Sunparadai'.

The new *Mandevilla* is a naturally-occurring branch mutation of the *Mandevilla hybrida* cultivar Sunmandecrim, disclosed in U.S. Plant Pat. No. 15,539. The new *Mandevilla* was discovered and selected by the Inventor from within a population of plants of the cultivar Sunmandecrim in a controlled environment in Amstelveen, The Netherlands in May, 2005.

Asexual reproduction of the new cultivar by cuttings in Leimuiderbrug, The Netherlands, since June, 2005, has shown that the unique features of this new *Mandevilla* are stable and reproduced true to type in successive generations.

SUMMARY OF THE INVENTION

Plants of the cultivar Sunparadai have not been observed under all possible environmental conditions. The phenotype may vary somewhat with variations in environment such as temperature and light intensity without, however, any variance in genotype.

The following traits have been repeatedly observed and are determined to be the unique characteristics of 'Sunparadai'. These characteristics in combination distinguish 'Sunparadai' as a new and distinct cultivar:

1. Upright and vining plant habit.
2. Relatively small glossy foliage.
3. Freely branching habit.
4. Freely flowering habit.
5. Dark red purple-colored flowers.
6. Long flowering period.

Plants of the new *Mandevilla* differ from plants of the parent, the cultivar Sunmandecrim, in the following characteristics:

1. Plants of the new *Mandevilla* have shorter stems with shorter internodes than plants of the cultivar Sunmandecrim.
2. Plants of the new *Mandevilla* have larger leaves than plants of the cultivar Sunmandecrim.
3. Plants of the new *Mandevilla* have larger flowers than plants of the cultivar Sunmandecrim.
4. Plants of the new *Mandevilla* and the cultivar Sunmandecrim differ in flower color as plants of the cultivar Sunmandecrim have red-colored flowers.

Plants of the new *Mandevilla* can be compared to plants of the *Mandevilla* cultivar Sunparasuji, disclosed in a U.S. Plant patent application Ser. No. 12/079,407. Plants of the new *Mandevilla* differ primarily from plants of the cultivar Sunparasuji in flower color as plants of the cultivar Sunparasuji have red-colored flowers with white-colored stripes.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the actual colors of the new *Mandevilla.*

The photograph at the top of the sheet comprises a side perspective view of a typical flowering plant of 'Sunparadai' grown in a container.

The photograph at the bottom of the sheet is a close-up view of a typical flower of 'Sunparadai'.

DETAILED BOTANICAL DESCRIPTION

In the following description, color references are made to The Royal Horticultural Society Colour Chart, 2001 Edition, except where general terms of ordinary dictionary significance are used. Plants used for the aforementioned photographs and following description were grown under conditions which closely approximate commercial production conditions during the late summer in an outdoor nursery in Higashiomi, Shiga, Japan for about four months. During the production of the plants, day temperatures averaged 25° C. and night temperatures averaged 15° C.

Botanical classification: *Mandevilla hybrida* cultivar Sunparadai.

Parentage: Naturally-occurring branch mutation of the *Mandevilla hybrida* cultivar Sunmandecrim, disclosed in U.S. Plant Pat. No. 15,539.

Propagation:

*Type.*—By vegetative cuttings.

*Time to initiate roots.*—About two weeks at 23° C. to 25° C.

Time to produce a rooted young plant.—About 40 days at 23° C. to 25° C.

*Root description.*—Fibrous, fleshy; light brown in color.

*Rooting habit.*—Freely branching.

Plant description:

*Form.*—Perennial. Upright and vining plant habit. Vigorous growth habit.

*Plant height.*—About 85 cm.

*Lateral branch description.*—Length: About 85 cm. Diameter: About 3 mm. Internode length: About 2 cm to 20 cm. Strength: Strong. Texture: Smooth, glabrous. Color, young: Close to 144B. Color, mature: Between N199B and N199D.

Foliage description:

*Arrangement.*—Opposite, simple.

*Length.*—About 6.2 cm.

*Width.*—About 4.8 cm.

*Shape.*—Broadly elliptic.

*Apex.*—Cuspidate.

*Base.*—Rounded.

*Margin.*—Entire.

*Texture, upper and lower surfaces.*—Smooth, glabrous.

*Luster, upper and lower surfaces.*—Glossy.

*Venation pattern.*—Pinnate, reticulate.

*Color.*—Developing and fully expanded foliage, upper surface: Close to 147A; venation, close to 144C. Developing and fully expanded foliage, lower surface: Close to 147C; venation, close to 144C.

*Petiole length.*—About 1.5 cm.

*Petiole diameter.*—About 1.8 mm.

*Petiole texture, upper and lower surfaces.*—Smooth, glabrous.

*Petiole color, upper and lower surfaces.*—Close to 144A.

Flower description:

*Flower type and habit.*—Single salverform flowers; flowers racemose; flowers face mostly outwardly. Freely flowering habit, about six flowers per inflorescence.

*Natural flowering season.*—Long flowering period; early summer to late autumn in Japan; flowering continuous during this period.

*Flower longevity on the plant.*—About seven to ten days. Flowers not persistent.

*Fragrance.*—Slightly fragrant; pleasant.

*Inflorescence length.*—About 15 cm.

*Inflorescence diameter.*—About 12 cm.

*Flowers.*—Appearance: Flared trumpet, corolla fused, five-parted; petals imbricate; flowers roughly star-shaped. Diameter: About 9.6 cm. Depth (length): About 6.8 cm. Throat diameter: About 1.8 cm. Tube length: About 4.6 cm. Tube diameter, mid-section: About 1.5 cm. Tube diameter, base: About 4.8 mm.

*Flower buds.*—Height: About 8 cm. Diameter: About 1.6 cm. Shape: Lenticular. Color: Close to 46A.

*Corolla.*—Arrangement/appearance: Single whorl of five petals, fused into flared trumpet; petals imbricate. Petal length: About 3.6 cm. Petal width: About 3.6 cm. Petal shape: Spatulate. Petal apex: Acute. Petal margin: Entire; curled outwardly; slightly undulate. Petal texture, upper and lower surfaces: Smooth, glabrous. Color: Petal, when opening, upper surface: Close to 53A. Petal, when opening, lower surface: Close to 53B. Petal, fully opened, upper surface: Close to 60B; color becoming closer to 60C with development. Petal, fully opened, lower surface: Close to 53B. Tube: Close to 53A to 53D; towards the base, close to 154D. Throat: Close to N25A.

*Sepals.*—Arrangement/appearance: Five per flower in a single whorl; fused. Length: About 9 mm. Width: About 2.2 mm. Shape: Lanceolate. Apex: Acute. Margin: Entire. Texture, upper and lower surfaces: Smooth, glabrous. Color, immature, upper and lower surfaces: Close to 145C; towards the apex, close to 46A. Color, mature, upper and lower surfaces: Close to 145C; towards the apex, close to 46A.

*Peduncles.*—Length: About 4.3 cm. Diameter: About 2.5 mm. Texture: Smooth, glabrous. Strength: Flexible, but strong. Color: Close to 143A.

*Pedicels.*—Length: About 1.8 cm. Diameter: About 1.4 mm. Texture: Smooth, glabrous. Strength: Flexible, but strong. Color: Close to 143A.

*Reproductive organs.*—Stamens: Quantity/arrangement: Typically five; filaments fused to corolla; anthers, connivent. Anther shape: Elliptic. Anther size: About 1 cm by 1.6 mm. Anther color: Close to 12D. Pollen amount: Scarce. Pollen color: Close to 155B. Pistils: Quantity: Typically one. Pistil length: About 3.3 cm. Stigma shape: Conical. Stigma color: Close to 144D. Style length: About 2.5 cm. Style color: Close to 155C. Ovary color: Close to 144C.

*Seed/fruit.*—Seed and fruit production has not been observed.

Disease/pest resistance: Plants of the new *Mandevilla* have not been noted to be resistant to pathogens and pests common to *Mandevilla*.

Temperature tolerance: Plants of the new *Mandevilla* have been observed to tolerate temperatures from about 4° C. to about 30° C.

It is claimed:

1. A new and distinct *Mandevilla* plant named 'Sunparadai' as illustrated and described.

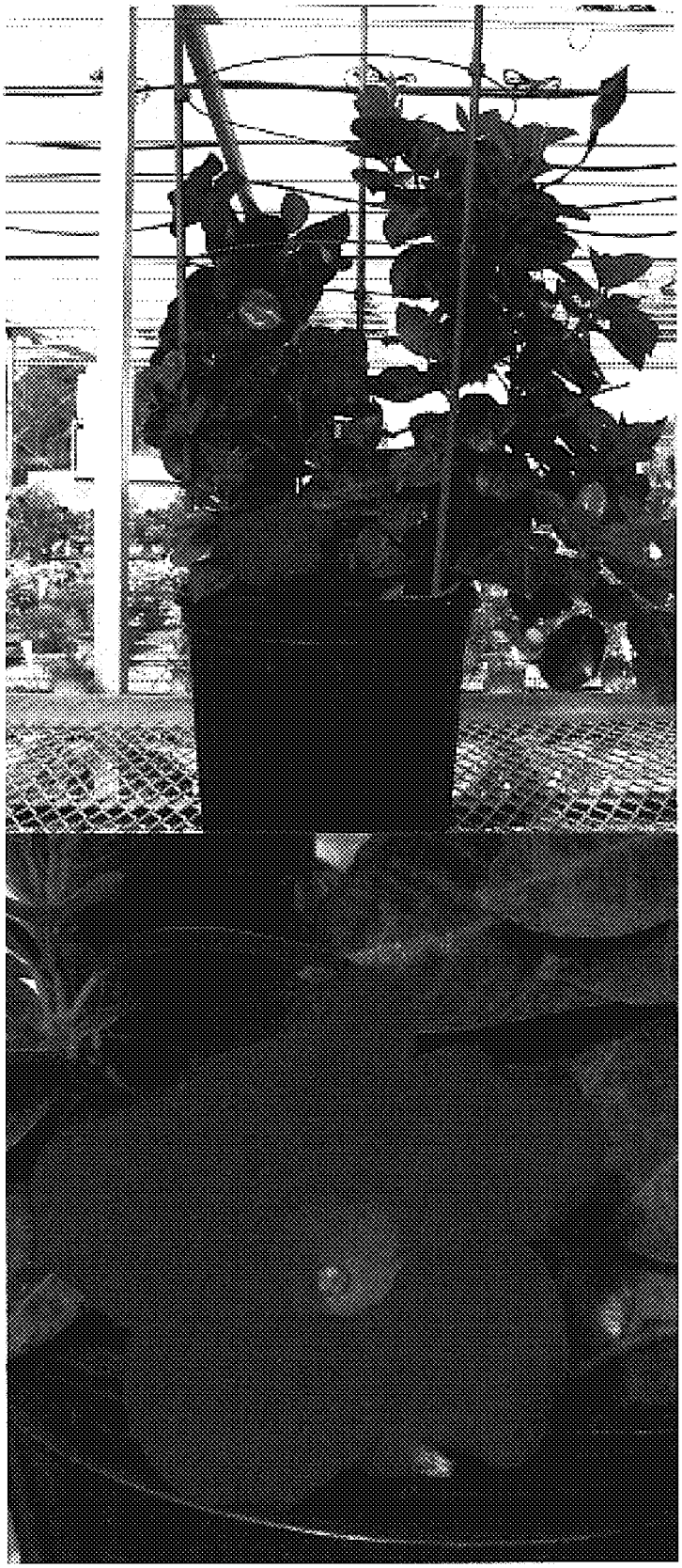

* * * * *